United States Patent [19]

Olthoff et al.

[11] Patent Number: 4,950,484
[45] Date of Patent: Aug. 21, 1990

[54] PHARMACEUTICAL TABLET, PHARMACEUTICAL GRANULATE AND PROCESS FOR THEIR PREPARATION

[75] Inventors: Margaretha Olthoff, Rijswijk; Leonardus W. T. De Boer, Hillegom; Piet J. Akkerboom, Zoetermeer, all of Netherlands

[73] Assignee: Gist-Brocades N.V., Delft, Netherlands

[21] Appl. No.: 162,834

[22] Filed: Mar. 2, 1988

[30] Foreign Application Priority Data

Mar. 2, 1987 [EP] European Pat. Off. ........ 87200357.9

[51] Int. Cl.$^5$ .......................... A61K 9/20; A61K 9/16
[52] U.S. Cl. ................... 424/464; 424/499; 424/501; 424/465
[58] Field of Search ............... 424/472, 489, 468, 494, 424/480, 465, 464, 499, 501

[56] References Cited

U.S. PATENT DOCUMENTS

| | | | |
|---|---|---|---|
| 3,870,790 | 3/1975 | Lowey et al. | 424/480 X |
| 4,292,299 | 9/1981 | Suzuki et al. | 424/472 X |
| 4,369,172 | 1/1983 | Schor et al. | 424/480 X |
| 4,389,393 | 6/1983 | Schor et al. | 424/480 X |
| 4,421,738 | 12/1983 | Yamagiwa et al. | 424/480 X |
| 4,428,951 | 1/1984 | Hata et al. | 424/480 X |
| 4,454,108 | 6/1984 | Iida et al. | 424/472 |
| 4,525,339 | 6/1985 | Behl et al. | 424/480 X |
| 4,654,206 | 3/1987 | Okuda et al. | 424/480 |
| 4,665,081 | 5/1987 | Doi et al. | 514/356 |
| 4,753,801 | 6/1988 | Oren et al. | 424/465 |
| 4,837,030 | 6/1989 | Valorose, Jr. et al. | 424/456 |
| 4,844,907 | 7/1989 | Elger et al. | 424/465 |
| 4,851,233 | 7/1989 | Khan et al. | 424/480 |

FOREIGN PATENT DOCUMENTS

| | | |
|---|---|---|
| 0049061 | 4/1982 | European Pat. Off. . |
| 0073428 | 3/1983 | European Pat. Off. . |
| 0080862 | 6/1983 | European Pat. Off. . |
| 0159735 | 10/1985 | European Pat. Off. . |
| 2251250 | 5/1974 | Fed. Rep. of Germany . |
| 2518270 | 3/1976 | Fed. Rep. of Germany . |
| 2058565 | 4/1981 | United Kingdom . |
| 2172006 | 9/1985 | United Kingdom . |

*Primary Examiner*—Thurman K. Page
*Attorney, Agent, or Firm*—Fleit, Jacobson, Cohn, Price, Holman & Stern

[57] ABSTRACT

A pharmaceutical tablet containing an amphoteric beta-lactam antibiotic, microcrystalline or micro fine cellulose or a mixture of both and a second disintegrant, being low-substituted hydroxypropylcellulose, which fully disintegrates in water within 60 seconds. When swallowed it shows a bioavailability as good as a pharmacy prepared suspension of the antibiotic. The tablet is compressed from a mixture containing a new granulate which is prepared from the antibiotic substance, microcrystalline and/or micro fine cellulose and water only. Such tablets can also be prepared by using other known tablet disintegrants as the second disintegrant.

22 Claims, No Drawings

PHARMACEUTICAL TABLET, PHARMACEUTICAL GRANULATE AND PROCESS FOR THEIR PREPARATION

The invention relates to a pharmaceutical composition comprising an amphoteric beta-lactam antibiotic. More particularly, the invention relates to a pharmaceutical tablet which disintegrates quickly when immersed in water and which, when ingested, provides a high bioavailability of antibiotic. The invention further relates to a process for the preparation of this tablet by wet granulation.

BACKGROUND OF THE INVENTION

The therapeutic action of a medicine in a living organism depends to a considerable extent on its formulation. When drugs are administered orally, high demands are made upon the pharmaceutical formulation.

The first demand is a high bioavailability: the medicine in the composition should be made available to the organism in as high an amount as possible and the optimum blood levels should be reached within the shortest possible time.

This is a typical demand in the treatment of infections with an antibiotic composition with which the present invention is concerned.

A second demand made upon pharmaceutical formulations is that it allows administration to the patient without problems. However, the formulation with the best bioavailability is seldom easy to use and on the other hand, one which is easy to use often does not have satisfactory bioavailability.

By way of example: amoxicillin is the most prescribed beta-lactam antibiotic. A considerable amount of amoxicillin is delivered as an aqueous suspension as this shows the best bioavailability. However, such suspensions have serious drawbacks: They have to be prepared by the pharmacist shortly before delivery to the patient. The suspension should be kept cool in a refrigerator because otherwise it is liable to deterioration. When administered it has to be measured with a spoon or a cup with inherent inaccuracy of the dosage volume. Another inconvenience to the patient is the discomfort caused by the sticky sugary liquid and the tacky container.

To overcome these drawbacks other dosage forms, e.g. capsules or tablets, have been made available. However, many patients have serious problems with swallowing such a solid dosage form, especially the larger ones. Moreover the bioavailability and maximum concentration of antibiotic in blood and the time wherein this concentration is reached are inferior to those of the aqueous suspension.

When developing a new pharmaceutical composition, particularly in tablet form, there is still a third category of requirements which has to be met: the ingredients should satisfy the demands of the pharmaceutical production process. Amoxicillin, for example, presents a very bad flow pattern and this, combined with its sensitivity to moisture, places serious restrictions on its formulation. It is also important that the tablet should possess appropriate physico-chemical properties relating to hardness, stability, friability, disintegration time and so on.

To meet these various requirements pharmacy has at its disposal a great variety of adjuvants subdivided as diluents, binders and adhesives, disintegrants, lubricants, glidants and flow promoters as well as colours, flavours and sweeteners. It is the task of pharmacy to develop pharmaceutical formulations which have certain specified properties. One of the common pharmaceutical operations is preparing intimate mixtures of several ingredients. These ingredients may interact with each other during formulation and therefore one cannot predict in detail the physico-chemical characteristics of the resulting pharmaceutical composition which may have surprising properties.

STATE OF THE ART

One way to improve the bioavailability of the antibiotic in tablets is to have them disintegrate faster when immersed in water. With the aid of disintegrants, dispersible tablets have been developed which disintegrate in a few minutes or less when immersed in water.

Belgian patent 817515 describes a tableted beta-lactam antibiotic which is said to disintegrate fast in the stomach. The mixture to be tableted contains the beta-lactam antibiotic and urea. Binders or diluents have been omitted because these appear to slow down the disintegration. The resulting tablet is said to disintegrate relatively fast, so that the active ingredient is liberated in about 13 minutes.

British patent 2084016 describes an amoxicillin containing tablet, which is prepared with two disintegrants, microcrystalline cellulose and either sodium starch glycolate or cross-linked polyvinylpyrrolidone. However, there is no mention of favourable disintegration behavior or of unexpectedly good absorption.

Dispersible tablets containing disintegrants form a special category. When put into a glass of water they disintegrate fast into a fine dispersion which can be subsequently ingested.

However, existing dispersible tablets for beta-lactam antibiotics are large with respect to the dose of antibiotic and do not show good disintegration behavior. A well known 500 mg amoxicillin containing tablet weighs 1260 mg. It disintegrates within 2 minutes and the dispersion contains coarse lumps.

SUMMARY OF THE INVENTION

After extensive experimentation, we have developed a tablet suited for amphoteric beta-lactam antibiotics which utilises the combination of the disintegrants, microcrystalline cellulose and low-substituted hydroxypropylcellulose.

Microfine cellulose may partially or fully substitute for the microcrystalline cellulose, without affecting the invention process or the properties of the invention products.

Such a tablet can either be easily swallowed as such or after being dispersed in water can be drunk. This formulation has a bioavailability of the antibiotic which equals that of the corresponding pharmacy prepared aqueous suspension and which is the same for the tablet either swallowed as such or drunk as a suspension.

These tablets may be prepared by compressing a granulate which is mixed with several adjuvants. The granulate contains the beta-lactam antibiotic and microcrystalline and/or microfine cellulose. No substantial amount of wet binder is present in the tablet, least less than 0.5 wt % preferably 0–0.1 wt % based on the weight of the antibiotic. A part of the microcrystalline and/or microfine cellulose is mixed with the active substance and granulated with water. The other part is admixed to the granulate together with a second disintegrant, preferably low-substituted hydroxypropylcellulose or cross-linked polyvinylpyrrolidon and, optionally, other adjuvants. The resulting mixture possesses a good flow and can be processed smoothly in the tableting press.

DETAILS OF THE INVENTION

The developed dispersible tablet contains an amphoteric beta-lactam antibiotic and two different disintegrants, one of which is a cellulose product, viz., microcrystalline cellulose or microfine cellulose or a mixture of both and the other one is low-substituted hydroxypropylcellulose. Microcrystalline cellulose is the common name for purified, partially depolymerized cellulose occurring as a crystalline powder composed of porous particles. It is a widely used adjuvant, known e.g. under the brand name AVICEL.

Low-substituted hydroxypropylcellulose (1-HPC) is the common name of cellulose which is partially substituted with 2-hydroxypropoxy groups. The substitution grade for the so-called low-substituted variant, a common pharmaceutical adjuvant, is less than 25% and preferably is 7-16%. Microfine cellulose (e.g. EL-CEMA), also denoted as powdered cellulose, is a mechanically processed alpha-cellulose from fibrous plant materials. It is a common pharmaceutical binder and disintegrant. In this description and the appended claims, "cellulose product" refers particularly to microcrystalline cellulose and microfine cellulose and to mixtures of them.

The invented tablet exhibits a new and valuable combination of outstanding properties. The most important and surprising one is that the bioavailability of the antibiotic when swallowed as such is as good as when it is dispersed in water before taking it. The amount of active substance absorbed into the blood is the same in both cases. The bioavailability equals that of the known pharmacy prepared aqueous suspensions. This bioavailability is demonstrated in the following data collected for a 500 mg amoxicillin-containing tablet in accordance with this invention:

|  | $C_{max}$ | $T_{max}$ | bioavailability (AUC) |
|---|---|---|---|
| invention tablet swallowed as such | 9.2 | 68 | 19.0 |
| invention tablet taken as a dispersion in water | 9.2 | 58 | 18.7 |
| known ready suspension | 9.5 | 61 | 17.8 |

$C_{max}$ is the maximum concentration of the antibiotic expressed in micrograms per ml of blood after administration.

$T_{max}$ is the time in minutes when the $C_{max}$ is attained.

The bioavailability is expressed as a number proportional with the area under the graphic curve (AUC) which graph represents the blood concentration progressing with time.

When immersed in water, the tablet of the invention fully disintegrates within 60 seconds into an excellent aqueous dispersion. However, its disintegration proceeds sufficiently slowly for swallowing it easily.

Since it is known from literature that a standard amoxicillin preparation shows a wide variation in bioavailability between individuals, it is surprising that the invention tablet exhibits only a small interindividual variation, irrespective whether the tablet was swallowed as such or drunk as an aqueous dispersion. This additional advantage could be a consequence of the much improved disintegration behavior of the tablet.

The tablets of the invention preferably contain 2-20 wt % of low-substituted hydroxypropylcellulose, more preferably 7-10 wt %, the percentage being based on the weight of antibiotic.

A further aspect of the invention is that only small amounts of disintegrants and other excipients are necessary which results in a considerably smaller tablet, which is easier to swallow, as compared with prior art dispersible tablets containing the same amount of antibiotic. A 500 mg amoxicillin containing tablet of the invention has a weight for example of 937 mg, whereas the comparable prior art tablet would weigh 1260 mg.

Therefore, according to another feature of the invention, the tablet contains a high percentage of active substance, which can be 20-70 wt %, but is preferably 50-65 wt %.

The fact that the tablet of the invention can be taken, at the patients choice, either as a solid tablet or as a liquid dispersion contributes to better patient compliance. There is a lower risk that the therapy fails because the patient is reluctant to take the prescribed medicine.

There is also an economic advantage in that only one dosage form needs to be produced and kept in store. Suspensions, capsules, sachets, effervescent tablets etc. become obsolete for the antibiotics which are formulated in accordance with this invention.

The new tablet satisfies all common pharmaceutical standards with respect to hardness, friability and stability. The disintegration time of the larger, high dose tablet is hardly any longer than that of the smaller, low dose tablet.

The tablet of the invention is designed for amphoteric beta-lactam antibiotics. Beta-lactam antibiotics comprise the penicillins and the cephalosporins. Amphoteric means that the molecule contains the same number of free amino groups as of free carboxyl groups. Examples are ampicillin, cefalexin and cefradin, but preferably amoxicillin is used. Usually amoxicillin trihydrate is employed.

The material for compressing consists of a granulate mixed with several adjuvants. The granulate contains the beta-lactam antibiotic and microcrystalline and/or microfine cellulose. A suitable amount of microcrystalline and/or microfine cellulose in the granulate is 20-50 wt %, preferably 35-45 wt % based on the weight of antibiotic. Microcrystalline and/or microfine cellulose, low-substituted hydroxypropylcellulose and optionally further adjuvants are then mixed with the granulate. A suitable further amount of microcrystalline and/or microfine cellulose is 4-20 wt %, preferably 8-15 wt % based on the weight of the antibiotic. A suitable amount of low-substituted hydroxypropylcellulose is 2-20 wt %, preferably 7-10 wt % based on the weight of the antibiotic.

A further aspect of the invention is a process for the preparation of tablets containing an amphoteric beta-lactam antibiotic together with two different disintegrants, one of which is a cellulose product, viz., microcrystalline cellulose or microfine cellulose or a mixture of both. The process comprises preparing a granulate, mixing the granulate with the further ingredients, and compressing the resulting mixture into tablets.

The necessary granulate is obtained using a process comprising the following steps:

The beta-lactam antibiotic is mixed with a part of the disintegrant microcrystalline and/or microfine cellulose as sole adjuvant and granulated with water. It is important that the remainder of the disintegrant is retained to be added to the granulate when formed.

The resulting wet mass is further treated in the usual way. The obtained granules are milled, dried, milled again and sieved. The wet granules are thoroughly dried in a fluidized bed dryer at a temperature of less than 70° C. and preferably less than 45° C.

The particle size distribution in the granulate appears to contribute to the disintegration behavior of the tablet. A suitable distribution is: 100% <0.7 mm, with not more than 30% (preferably 10%) <0.5 mm and not more than 50% (preferably 20–40%) <0.15 mm.

A good granulate is obtained which can be easily processed, and shows an excellent disintegration pattern. This is surprising because microcrystalline cellulose, when used in wet granulation, according to the prior art, is always combined with another adjuvant, particularly the binder lactose. Moreover for beta-lactam antibiotics, especially amoxicillin, wet granulation is avoided in the prior art because these antibiotics are generally moisture sensitive.

The resulting granulate is then mixed with the remaining part of the microcrystalline and/or microfine cellulose, the second disintegrant and optionally, other adjuvants and compressed into tablets. Usual other adjuvants are lubricants as magnesium stearate, flow promoters as colloidal silica and flavours and sweeteners.

The quality of the granulate is best when using 20–50 wt % of microcrystalline and/or microfine cellulose, preferably 35–45 wt %, mixed with 40–80 wt % of water, preferably 50–70 wt %, all percentages with respect to the weight of the antibiotic.

It is a further advantage of the invention that an organic solvent, with all its safety hazards, as granulation liquid is avoided.

The proportion of granulate used in the tableting mixture is such that the total mixture contains 20–70 wt %, preferably 50–65 wt % of the antibiotic.

The amount of microcrystalline and/or microfine cellulose added to the granulate is 4–20 wt %, preferably 8–15 wt % based on the weight of antibiotic.

The use of the second disintegrant in the tableting mixture is essential for proper disintegration behavior of the tablet. The optimum disintegrating behavior is achieved when 2–20 wt %, preferably 7–10 wt % of the second disintegrant is used, based on the weight of the antibiotic. Examples of compounds which can be used as the second disintegrant are cross-linked polyvinylpyrrolidone (e.g. Kollidon CL), cross-linked sodium carboxymethylcellulose (e.g. Ac-Di-Sol), starch or starch derivatives such as sodium starch glycolate (e.g. Explotab), or combinations with starch (e.g. Primojel), swellable ion-exchange resins, such as Amberlite IRP 88, formaldehyd-casein (e.g. Esma Spreng), alginates, but preferably the second disintegrant is low-substituted hydroxypropylcellulose or cross-linked polyvinylpyrrolidone. The former substance also enhances the cohesiveness of the tablet.

A further characteristic of the invention is that wet binders are avoided in the tablet. These substances, used for their binding properties in wet granulation, in amounts of about 1–10 wt % based on the weight of the active substance, comprise acacia gum, gelatin, polyvinylpyrrolidone, starch (paste and pre-gelatinized), sodium alginate and alginate derivatives, sorbitol, glucose and other sugars, tragacanth, and soluble celluloses like methylcellulose, hydroxypropylmethylcellulose and hydroxypropylcellulose. If present, their amount is less than 0.5 wt %, preferably 0–0.1 wt % based on the weight of the antibiotic.

The process is suited for all amphoteric beta-lactam antibiotics but is most advantageously applied for amoxicillin.

The invention is further illustrated by the following examples, which should not be conceived to be a limitation of the invention.

Reported disintegration times have been measured according to Example 39.

EXAMPLE 1

Granulate containing amoxicillin

| Amoxicillin trihydrate | 720 g |
|---|---|
| Microcrystalline cellulose | 288 g |
| Water | 420 ml |

The solid components were mixed thoroughly and granulated with the water. The wet mass was kneaded for 20 minutes, then milled and dried with air of 70° C. in a fluidized bed drier until the granulate contained not more than 10.5% of water. The dried granules were passed through a 0.8 mm sieve and collected.

EXAMPLE 2

Granulate containing amoxicillin

| Amoxicillin trihydrate | 750 g |
|---|---|
| Microcrystalline cellulose | 150 g |
| Water | 345 ml. |

A granulate was obtained from these components by following the procedure of Example 1.

EXAMPLE 3

Tablets containing amoxicillin

| Granulate from Example 1 | 500 g |
|---|---|
| Microcrystalline cellulose | 30 g |
| Low-substituted hydroxypropylcellulose | 20 g |
| Saccharin | 3.5 g |
| Flavours | 4.0 g |
| Colloidal silica | 1.5 g |
| Magnesium stearate | 7.5 g |

The granulate was mixed for 10 minutes with the other excipients, after which the obtained mixture was compressed into tablets on a rotary press. The characteristics of tablets with various amounts of amoxicillin were:

| dosage amoxicillin (as free acid) | weight | diameter | hardness | disintegration time |
|---|---|---|---|---|
| 125 mg | 234 mg | 9 mm | 137 N | 30 sec |
| 250 mg | 469 mg | 11 mm | 98 N | 50 sec |
| 500 mg | 937 mg | 15 mm | 137 N | 35 sec |
| 1000 mg | 1874 mg | 20 mm | 137 N | 45 sec |

EXAMPLE 4

Tablets containing amoxicillin

| | |
|---|---|
| Granulate from Example 2 | 600 g |
| Microcrystalline cellulose | 100 g |
| Low-substituted hydroxypropylcellulose | 50 g |
| Saccharin | 9 g |
| Flavours | 11 g |
| Colloidal silica | 1.5 g |
| Magnesium stearate | 7.5 g |

Tablets were obtained from these components by following the procedure of Example 3. Tablets with varying dosage levels of amoxicillin may be prepared. The 1000 mg amoxicillin tablet for example has a weight of 1830 mg, a hardness of 137N and it disintegrates within 60 seconds in water.

EXAMPLES 5-10

Tablets containing amoxicillin

| | |
|---|---|
| Granulate from Example 1 | 100 g |
| Microcrystalline cellulose | 6.18 g |
| Disintegrant (see Table below) | 6.18 g |
| Colloidal silica | 0.19 g |
| Magnesium stearate | 0.93 g |

Tablets containing about 592 mg amoxicilin trihydrate were obtained from these components by following the procedure of Example 3.

Depending on the specific disintegrant the resulting tablets showed the following characteristics:

| Example | Disintegrant | Weight | Hardness | Disintegration time |
|---|---|---|---|---|
| 5 | Amberlite IRP 88 | 939 mg | 105 N | 60 sec |
| 6 | Potato starch | 964 mg | 113 N | 57 sec |
| 7 | Kollidon CL | 955 mg | 107 N | 26 sec |
| 8 | Esma Spreng | 925 mg | 123 N | 56 sec |
| 9 | Explotab | 939 mg | 119 N | 51 sec |
| 10 | L-HPC | 925 mg | 103 N | 33 sec |

Friability: 0.2-0.4%

EXAMPLE 11

Granulate containing cefalexin monohydrate

| | |
|---|---|
| Cefalexin monohydrate | 720 g |
| Microcrystalline cellulose | 288 g |
| Water | 420 ml |

A granulate was obtained from these components by following the procedure of Example 1.

EXAMPLES 12-19

Tablets containing cefalexin monohydrate

| | |
|---|---|
| Granulate from Example 11 | 50 g |
| Microcrystalline cellulose | 3.09 g |
| Disintegrant (see Table below) | 3.09 g |
| Colloidal silica | 0.10 g |
| Flavours | |
| Apricot | 0.56 g |
| Vanillin | 0.06 g |
| Saccharin | 0.56 g |
| Magnesium stearate | 0.470 g |

Tablets containing about 500 mg cefalexin monohydrate were obtained from these components by following the procedure of Example 3. Depending on the specific disintegrant the resulting tablets showed the following characteristics:

| Example | Disintegrant | Weight | Hardness | Disintegration time |
|---|---|---|---|---|
| 12 | Amberlite IRP 88 | 817 mg | 100 N | 30 sec |
| 13 | Potato starch | 819 mg | 120 N | 30 sec |
| 14 | Ac-Di-Sol | 811 mg | 110 N | 40 sec |
| 15 | Kollidon CL | 812 mg | 120 N | 30 sec |
| 16 | Esma Spreng | 813 mg | 90 N | 55 sec |
| 17 | Explotab | 810 mg | 130 N | 35 sec |
| 18 | Primojel | 813 mg | 130 N | 40 sec |
| 19 | L-HPC | 811 mg | 120 N | 30 sec |

Friability: less than 1%

EXAMPLE 20

Granulate containing ampicillin anhydrate

| | |
|---|---|
| Ampicillin anhydrate | 720 g |
| Microcrystalline cellulose | 288 g |
| Water | 420 ml |

A granulate was obtained from these components by following the procedure of Example 1.

EXAMPLES 21-25

Tablets containing ampicillin anhydrate

| | |
|---|---|
| Granulate from Example 20 | 50 g |
| Microcrystalline cellulose | 3.09 g |
| Disintegrant (see Table below) | 3.09 g |
| Colloidal silica | 0.10 g |
| Flavours | |
| Apricot | 0.56 g |
| Vanillin | 0.06 g |
| Saccharin | 0.56 g |
| Magnesium stearate | 0.470 g |

Tablets containing about 480 mg ampicillin anhydrate were obtained from these components by following the procedure of Example 3. Depending on the specific disintegrant the resulting tablets showed the following characteristics:

| Example | Disintegrant | Weight | Hardness | Disintegration time |
|---|---|---|---|---|
| 21 | Ac-Di-Sol | 782 mg | 90 N | 43 sec |
| 22 | Kollidon CL | 777 mg | 90 N | 30 sec |
| 23 | Explotab | 786 mg | 89 N | 45 sec |
| 24 | Primojel | 785 mg | 101 N | 44 sec |
| 25 | L-HPC | 766 mg | 100 N | 44 sec |

Friability: 0.1-0.2%

EXAMPLE 26

Granulate containing ampicillin trihydrate

| | |
|---|---|
| Ampicillin trihydrate | 720 g |
| Microcrystalline cellulose | 288 g |
| Water | 470 ml |

A granulate was obtained from these components by following the procedure of Example 1.

EXAMPLES 27-34

Tablets containing ampicillin trihydrate

| | |
|---|---|
| Granulate from Example 26 | 50 g |
| Microcrystalline cllulose | 3.09 g |
| Disintegrant (see Table below) | 3.09 g |
| Colloidal silica | 0.10 g |
| Flavours | |
| Apricot | 0.56 g |
| Vanillin | 0.06 g |
| Saccharin | 0.56 g |
| Magnesium stearate | 0.470 g |

Tablets containing about 555 mg ampicillin trihydrate were obtained from these components by following the procedure of Example 3. Depending on the specific disintegrant the resulting tablets showed the following characteristics:

| Example | Disintegrant | Weight | Hardness | Disintegration time |
|---|---|---|---|---|
| 27 | Amberlite IRP 88 | 910 mg | 88 N | 53 sec |
| 28 | Potato starch | 931 mg | 115 N | 41 sec |
| 29 | Ac-Di-Sol | 906 mg | 102 N | 46 sec |
| 30 | Kollidon CL | 902 mg | 91 N | 21 sec |
| 31 | Esma Spreng | 893 mg | 90 N | 42 sec |
| 32 | Explotab | 890 mg | 99 N | 33 sec |
| 33 | Primojel | 913 mg | 103 N | 28 sec |
| 34 | L-HPC | 897 mg | 103 N | 24 sec |

EXAMPLE 35

Granulate containing cefradin

| | |
|---|---|
| Cefradin | 720 g |
| Microcrystalline cellulose | 288 g |
| Water | 635 ml |

A granulate was obtained from these components by following the procedure of Example 1.

EXAMPLES 36-38

Tablets containing cefradin

| | |
|---|---|
| Granulate from Example 35 | 50 g |
| Microcrystalline cellulose | 3.09 g |
| Disintegrant (see Table below) | 3.09 g |
| Colloidal silica | 0.10 g |
| Flavours | |
| Apricot | 0.56 g |
| Vanillin | 0.06 g |
| Saccharin | 0.56 g |
| Magnesium stearate | 0.470 g |

Tablets containing about 500 mg cefradin were obtained from these components by following the procedure of Example 3. Depending on the specific disintegrant the resulting tablets showed the following characteristics:

| Example | Disintegrant | Weight | Hardness | Disintegration time |
|---|---|---|---|---|
| 36 | Kollidon CL | 888 mg | 108 N | 32 sec |
| 37 | Explotab | 881 mg | 107 N | 60 sec |
| 38 | L-HPC | 879 mg | 111 N | 62 sec |

Friability: 0.5%

EXAMPLE 39

Measurement of the tablet disintegration time

The tablet to be tested is immersed in 50 ml of water of 20° C. After 30 sec the vessel is swinged so that the liquid starts whirling and not yet disintegrated lumps become visible. As soon as all large lumps have disappeared time is read and the suspension is poured through a 0.71 mm sieve. The reported values are the average of at least two measurements.

EXAMPLE 40

200 g of amoxicillin trihydrate were mixed with 80 g of microfine cellulose (ELCEMA G400) and 150 ml of water. The resulting wet mass was kneaded for 20 minutes, sieved through a 2 mm mesh sieve and dried in a fluidized bed dryier at about 60° C. during about one hour until the granulate contained not more than 10.5 wt % of water. The obtained dry granulate was sieved through a 0.8 mm sieve and collected.

EXAMPLE 41

| | | |
|---|---|---|
| 50 | g | granulate from Example 40 |
| 3.09 | g | microfine cellulose (ELCEMA G400) |
| 3.09 | g | 1-HPC |
| 0.1 | g | colloidal silca |
| 0.56 | g | saccharin |
| 0.62 | g | flavours |
| 0.47 | g | magnesium stearate |

The granulate was mixed for 10 minutes with the other excipients, after which the obtained mixture was compressed into tablets on a rotary press. The prepared 960 mg tablets had a hardness of 106N and disintegrated in water within 40 seconds.

We claim:

1. Pharmaceutical tablet comprising a mixture of an amphoteric beta-lactam antibiotic, and as disintegrants, low-substituted hydroxyproylcellulose and a cellulose product selected from the group consisting of microcrystalline cellulose, microfine cellulose and mixtures thereof.

2. Tablet according to claim 1 comprising 24-70 wt % of the cellulose product and 2-20 wt % of low-substituted hydroxypropylcellulose, the percentages being based on the weight of the antibiotic.

3. Tablet according to claim 1, characterized in that 0 wt % up to 0.1 wt % of a wet binding substance is present, based on the weight of the antibiotic.

4. Tablet according to claim 1, characterized in that it contains 20-70 wt % of the antibiotic, based on the weight of the tablet.

5. Pharmaceutical granulate comprising an amphoteric beta-lactam antibiotic, up to 0.5 wt % of a wet binding substance, based on the weight of the antibiotic, and a cellulose product selected from the group consisting of microcrystalline cellulose, microfine cellulose and mixtures thereof.

6. Granulate according to claim 5, characterized in that it contains 20-50 wt % of the cellulose product based on the weight of the antibiotic.

7. Process for the preparation of a granulate containing an amphoteric beta-lactam antibiotic, comprising
   (a) mixing an amphoteric beta-lactam antibiotic with water and a cellulose product selected from the group consisting of microcrystalline cellulose, microfine cellulose and mixtures thereof, and granulating the resulting wet mass to form a granulate; and (b) milling, drying, milling and sieving the granulate.

8. Process according to claim 7, characterized in that the mixture to be granulated contains 20-50 wt % of the cellulose product based on the weight of the antibiotic.

9. Process according to claim 7, characterized in that the mixture to be granulated contains 35-45 wt % of the cellulose product based on the weight of the antibiotic.

10. Process according to claim 7, characterized in that the mixture to be granulated contains 0 wt % up to 0.1 wt % of a wet binding substance, based on the weight of the antibiotic.

11. Process for the preparation of a tablet containing an amphoteric beta-lactam antibiotic, comprising
(a) mixing the granulate according to claim 5 with an additional amount of the cellulose product and a second disintegrant; and
(b) tableting the mixture.

12. Process according to claim 11 characterized in that the tableting mixture contains 50-65 wt % of the antibiotic based on the weight of the mixture.

13. Process according to claim 11, characterized in that the second disintegrant is low-substituted hdyroxypropylcellulose.

14. Process according to claim 11, characterized in that the second disintegrant is cross-linked polyvinylpyrrolidone.

15. Process according to claim 11, characterized in that the additional amount of the cellulose product is 4-20 wt %, based on the weight of the antibiotic.

16. Process according to claim 11, characterized in that the second disintegrant is low-substituted hydroxypropylcellulose or cross-linked polyvinylpyrrolidone and the granulate is mixed with 2-20 wt % of the second disintegrant, based on the weight of the antibiotic.

17. Granulate according to claim 5, characterized in that it comprises 0 wt % up to 0.1 wt % of a wet binding substance, based on the weight of the antibiotic.

18. A tablet according to claim 1 comprising 43-60 wt % of the cellulose product and 7-10 wt % of low-substituted hydroxypropylcellulose, based on the weight of the antibiotic.

19. A tablet according to claim 1, characterized in that it contains 50-65 wt % of the antibiotic, based on the weight of the tablet.

20. Granulate according to claim 5, characterized in that it contains 35-45 wt % of the cellulose product based on the weight of the antibiotic.

21. Process according to claim 11, characterized in that the additional amount of the cellulose product is 8-15 wt %, based on the weight of the antibiotic.

22. Process according to claim 16, characterized in that the granulate is mixed with 7-10 wt % of the second disintegrant, based on the weight of the antibiotic.

* * * * *